United States Patent [19]

Kegelman et al.

[11] Patent Number: 5,776,784
[45] Date of Patent: Jul. 7, 1998

[54] APPARATUS AND METHOD FOR REAGENT SEPARATION IN A CHEMICAL ANALYZER

[75] Inventors: Joseph Edward Kegelman; Diane Kathleen Stille, both of Wilmington; Robert Kyle Wiedenmann, New Castle, all of Del.; Paul John Zuk, Lincoln University, Pa.

[73] Assignee: Dade International Inc., Deerfield, Ill.

[21] Appl. No.: 585,333

[22] Filed: Jan. 11, 1996

[51] Int. Cl.⁶ ................................................. G01N 33/553
[52] U.S. Cl. .................... 436/526; 436/518; 436/815; 435/7.92
[58] Field of Search ............................ 436/526, 518, 436/815; 435/7.92

[56] References Cited

U.S. PATENT DOCUMENTS

| 4,628,037 | 12/1986 | Chagnon et al. | 436/526 |
|---|---|---|---|
| 4,661,408 | 4/1987 | Lau et al. | 428/405 |
| 4,672,040 | 6/1987 | Josephson | 436/526 |
| 4,698,302 | 10/1987 | Whitehead et al. | 435/94 |
| 4,916,081 | 4/1990 | Kamada et al. | 436/526 |
| 5,128,103 | 7/1992 | Wang et al. | 422/64 |
| 5,147,529 | 9/1992 | Lee et al. | 210/695 |
| 5,318,914 | 6/1994 | Matte et al. | 436/526 |

FOREIGN PATENT DOCUMENTS 6-213900  8/1994  Japan.

*Primary Examiner*—Marian C. Knode
*Assistant Examiner*—Donna C. Wortman
*Attorney, Agent, or Firm*—Leland K. Jordan

[57] ABSTRACT

Assays for separating magnetic particles include separating magnetically responsive particles from a liquid dispersion disposed in a plurality of reaction vessels, and transporting the reaction vessels in sequence past at least one processing position. A robotics reagent arm and probe dispense reagents into the reaction vessels and a reaction monitoring device is capable of relative movement with respect to the transporting device. Incomplete separation is effected by positioning a magnetic field in contact with the reaction vessel for a first shortened time interval during which the particles partially aggregate and afterwards are removed from the reaction vessel. The magnet is repositioned in contact with the reaction vessel for a third time interval to achieve full separation of particles from the liquid.

9 Claims, 5 Drawing Sheets

5,776,784

1

APPARATUS AND METHOD FOR REAGENT SEPARATION IN A CHEMICAL ANALYZER

BACKGROUND OF THE INVENTION

1. Field of the Invention

The present invention pertains to an apparatus and method for separating reagents during chemical analysis. More particularly, it relates to magnetic separation useful in heterogeneous medical diagnostic assays performed on an automatic chemical analyzer.

2. Description of the Related Art

It is well known to assay for antigens, blood analytes and other target substances present in a liquid sample using reactions involving a labeled reagent. One well known assay, the heterogeneous assay, requires a separation of an analyte-of-interest from potentially interfering substances. Accordingly, the steps of separation, isolation and concentration are taken to remove the interfering substances so that the assay can be performed. The "separation" can be performed several ways including solvent extraction, resin exchange and magnetic separation. In magnetic separation, the analyte-of-interest is attached or bound to magnetic particles which permit it to be isolated from fluids in a test or reaction vessel or concentrated within the test or reaction vessel using an externally applied magnetic field.

Two primary types of heterogeneous immunoassays are competitive immunoassays and sandwich immunoassays. In a competitive assay, an antibody to a sought-for antigen in a patient sample is contained in a first reagent and is attached to a derivatized magnetic particle to form a solid phase. A second reagent, consisting of a known amount of antigen attached to a tag (a measurable entity, including radioactive molecules, fluorescent molecules, or enzymes) and a patient sample are mixed with the solid phase in a test or reaction vessel. In the absence of antigen within the patient sample, about 50% of the antigen-tag is bound to the antibody of the magnetic solid phase. In the presence of patient antigen within the patient sample, some of the antibodies are coupled with patient antigen and are thereby unavailable to the tag antigen. As a result increasing amounts of patient antigen leads to decreasing amount of tag antigen. A calibration process is normally performed to correlate between the amount of patient antigen and the amount of measured tag. The separation step permits measuring the free tag or the bound tag, and not the total tag. Magnetic particles facilitate this separation when subjected to an externally applied magnetic field by combining particles with the bound tag into a pellet localized typically on the side of a reactor vessel. The free tag is then removed without interference from the magnetized pellet, for example by aspiration of the fluids from the reaction vessel. To complete the assay, a measuring reagent is added, the measuring reagent selected to enable measurement of the amount of bound tag. In a typical case, an enzyme may be used as the tag so that the reagent added is a "substrate" for the enzyme permitting the photometer measurement of the amount of color of the fluids in the reaction vessel tag that was bound to antibody.

In a typical sandwich immunoassay, antibodies to a sought-for antigen are attached to magnetic particles at a high concentration relative to the amount of antigen in a sample. Antigens are captured by antibodies on the magnetic particles and then the particles (and captured patient antigen) are separated from interfering substances in the sample. A second reagent, containing a second antibody to the sought-for antigen and having an attached tag, is added. The second antibody attaches to the patient antigen, previously captured by the first antibody on the magnetic particle, resulting in the formation of a sandwich. The second antibody tag is thus held firmly by the antigen to the first antibody on the magnetic particle. A magnetic separation similar to that described above permits the determination of bound tag which is in proportion to the patient antigen, the excess tag of the second reagent having been removed by aspiration.

Immunoassays using magnetic particles as a solid support are described for example in U.S. Pat. No. 4,661,408, U.S. Pat. No. 4,628,037, U.S. Pat. No. 4,672,040, and U.S. Pat. No. 4,698,302. The methods disclosed in these patents relate to manual magnetic separation processes and are relatively slow, require relatively strong magnets which are expensive, require considerable manual dexterity, and require an excessive amount of time to effect the separation with the purity required, particularly for sandwich type heterogeneous immunoassay.

U.S. Pat. No. 5,147,529 addresses the need to increase the efficiency of magnetic separation by exposing an aqueous dispersion of magnetic particles to a series of about 15 magnets of opposing polarity. The dispersion is contained in a reaction vessel and sequentially transported adjacent the magnets, the magnets being positioned at different heights in at least two consecutive processing positions relative to the longitudinal axis of the vessel. The difference in height facilitates separating the particles first from the bottom portion of the vessels and then from the upper regions of the vessels. The use of multiple magnets to affect such a separation disadvantageously requires additional time to subject the reaction vessel to the several magnets and to the system costs.

Another known automated heterogeneous magnetic immunoassay system combines reagents in a continuous flow stream where they are reacted together. The stream is then passed through a magnetic field where the magnetic particles are captured and the bound tag measured. A problem with continuous flow systems is carryover from one sample to the next which tends to produce erroneous results. This error is reduced by decreasing the number of samples analyzed per hour. Unfortunately, this adversely affects system throughput.

Automated magnetic particle separation systems have also been adapted onto chemical analyzers like the Dimension® Clinical Chemistry System as described in U.S. Pat. No. 5,128,103 sold by E. I. Du Pont, Wilmington, Del. A pair of robotics arms operating in conjunction with an assay wheel provides a transport means for the reaction vessels, the reaction vessels use chromium dioxide magnetic particles as the solid support. The reaction vessels are positioned sequentially in such fashion that magnetic separation occurs in a vessel next adjacent a photometric measuring apparatus. Consequently the photometric measuring apparatus is constrained from other activities during separation for a period of time required for magnetic separation, about 30 seconds, prior to analysis. This period of inactivity during magnetic separation as well as the relatively long time period for separation has an adverse impact on overall throughput or productivity with the chemical analyzer. Furthermore, during routine operation of the analyzer, the permanent magnet is passed multiple times closely proximate the reaction vessels and the multiple exposures of the vessels to the accompanying magnetic field can have a deleterious effect upon the reactions therein.

SUMMARY OF THE INVENTION

The present invention addresses many of the problems of the prior art analysis systems using magnetic particles as a separable solid support in heterogeneous assays. The invention provides means for increasing the efficiency of separating magnetic particles from fluid compositions in such immunoassays. This is done by subjecting the vessel to a magnetically effective magnetic field for a first time interval that is less than the time interval required to effect a complete separation of the particles from the dispersion. After the first time interval, the vessel is subjected to a magnetically ineffective magnetic field for a second time interval. Thereafter, the vessel is again subjected to a magnetically effective magnetic field for a third time interval greater than a time interval required to effect a complete separation of the particles from the dispersion.

The invention also provides an apparatus for separating magnetically responsive particles from a liquid dispersion disposed in a reaction vessel, the apparatus comprising transporting means for transporting the vessel to a processing position, a robotics arm comprising a reagent arm and a reagent probe adapted to provide analysis reagents to the reaction vessel, means for subjecting the vessel to a magnetically effective magnetic field for a first time interval, means for subjecting the vessel to a magnetically ineffective magnetic field for a second time interval, and means for subjecting the vessel to a magnetically effective magnetic field for a third time interval.

In a preferred embodiment, said first time interval is less than a time interval required to effect a complete separation of the particles from the dispersion. In another embodiment, said third time interval is greater than a time interval required to effect a complete separation of the particles from the dispersion.

This method and apparatus enhance the ability of the magnet 52 to position the particles such that magnetic separations can typically be achieved in far less time than those of the prior art with less complex equipment. In addition, because of the time cycles, the assay system is free to perform additional and/or unrelated functions thereby improving system throughput.

BRIEF DESCRIPTION OF THE DRAWINGS

The invention will be better understood with reference to the several drawings, in which like reference numerals are used to indicate like components, in which.

DETAILED DESCRIPTION OF THE PREFERRED EMBODIMENTS

Figure 1:
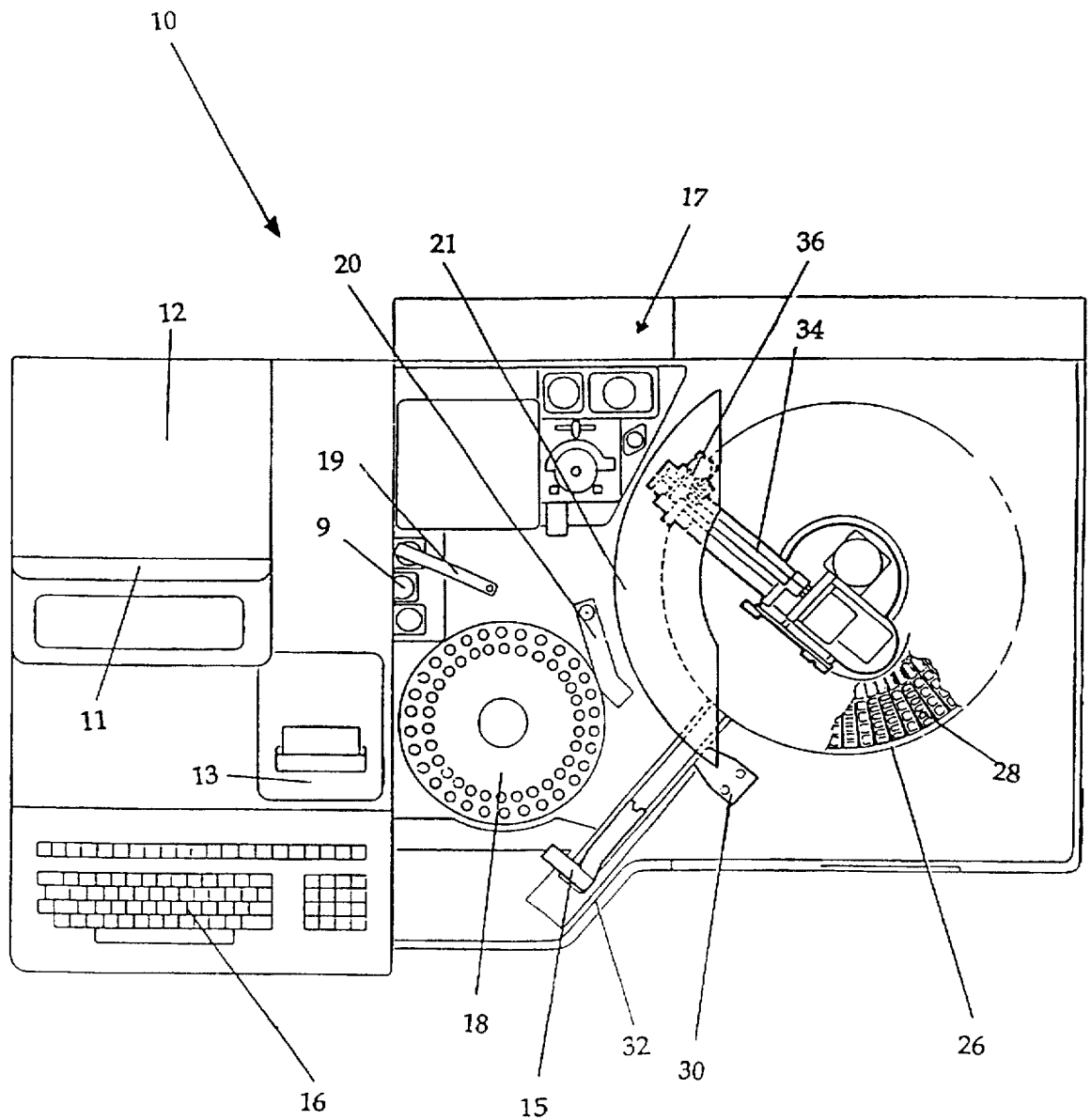
FIG. 1 is a pictorial plan view of an automatic clinical chemistry system in which this invention may find use.

FIG. 1 illustrates an automated clinical chemistry system 10 in which this invention may be used to advantage. System 10 includes a computer 12 with an appropriate display means 11 and keyboard 16 used to control all aspects of the system's operation. Such operations include system quality control, sample analysis, and generally controlling all active devices within the system 10 including a printout means 13 and a display means 11 of test results. A reagent tray 26 cooperates with a robotics arm comprising a reagent arm 34 and a reagent probe 36 described herein to provide analysis reagents. Sub-analysis modules 17, for instance useful for measuring fluid ionic content and comparing with standard fluids, contained in wells 9 and supplied by a fluid arm 19 to the module 17, may be included. Analytical portions of the system are normally enclosed in a temperature chamber 21 shown in portion for simplicity.

Figure 2:
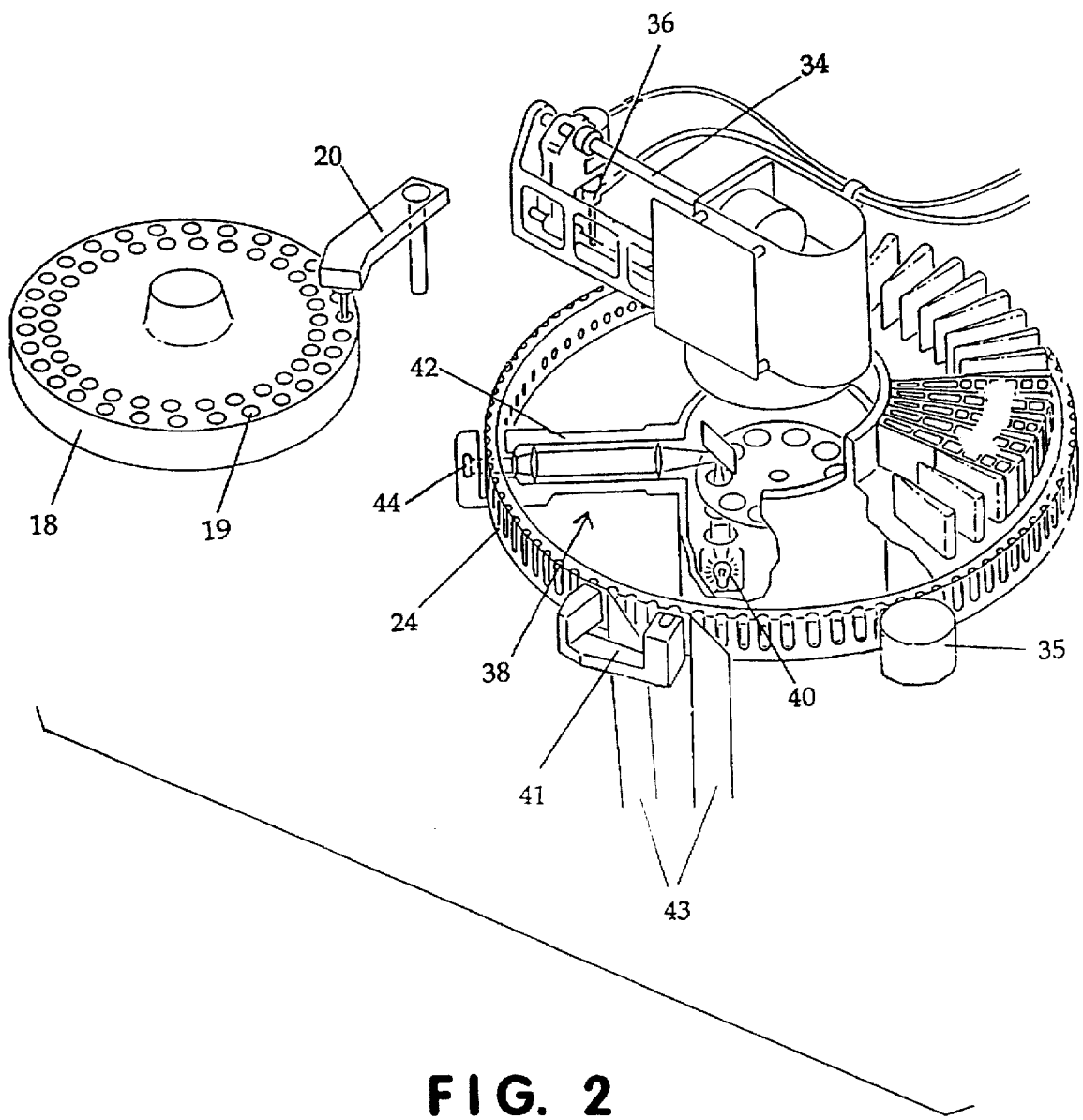
FIG. 2 is a partial, pictorial perspective view of a sample wheel and arm assembly, a reagent arm and probe, and transport means of an automatic clinical chemistry system in which this invention may find use.

FIG. 2 shows a sample carousel 18, having a plurality of sample wells 19, which is disposed relative to a rotatable sample arm 20 to transfer samples contained in sample wells 19 to a reaction vessel 22 (FIG. 5) supported on reaction vessel transport means 24 preferably adapted as a reaction vessel wheel 24. Reagent tray 26 (FIGS. 1 and 4) is disposed beneath reaction vessel wheel 24 and is adapted to support a plurality of reagent cartridges 28, best seen in FIG. 3, which contain various analysis reagents in either liquid or tablet form. Reagent cartridge 28 carries a bar code which is read by bar code reader 30 to correlate within computer 12 the reagent contents and location as the cartridges 28 are introduced onto the reagent tray 26 via a reagent shuttle 32. A cartridge follower 15 is provided to assist loading of reagent cartridges 28.

Figure 4:
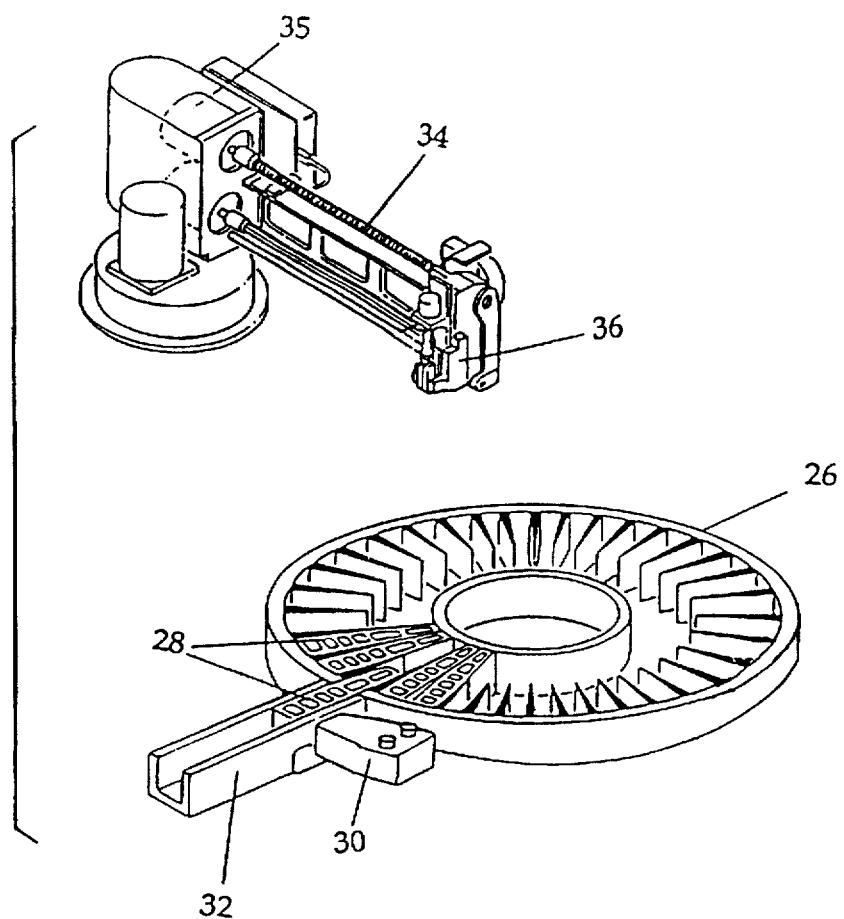
FIG. 4 is a pictorial perspective view of a support for the reagent supply of FIG. 3.

FIG. 4 illustrates a robotic reagent arm 34 which acts in cooperation with a probe 36 to access any one reagent cartridge 28 and aspirate and dispense reagent into reaction vessels 22 (FIG. 5) at any position around the reaction vessel transport means 24. Stepping motors 35 rotate reagent arm 34 and position reagent probe 36 to access any other reagent cartridges 28 to hydrate, mix and transfer other reagents from other appropriate reagent cartridges 28 as required to be used in analytical tests, preferably photometric tests. Reagent probe 36 is preferably a ultrasonic mechanism used for hydrating, aspirating, dispensing and mixing reagents.

Reaction vessels 22 may be supplied, as in the Dimension™ Instrument sold by E. I. du Pont de Nemours and Company, Wilmington, Del. by pulling two ribbons 43 of clear polymeric film from a reaction vessel film cartridge (not shown) onto the periphery of the reaction vessel transport means 24, shaping and sealing the ribbons with a molder 43 to form each reaction vessel 22. Reaction vessel wheel 24 has about 100 separate reaction vessels 22 created, as described in U.S. Pat. No. 5,128,103 and assigned to the assignee of the present invention. After the reaction vessels 22 are formed, sample arm 20 draws a sample from a sample well 19 in the sample carousel 18 and adds it to a reaction vessel 22. As described above, reagent arm 34 and probe 36 act to provide reagents as they are needed to reaction vessels 22 and mix the sample and reagents together. In another embodiment, a second reagent arm and probe (not shown) are provided to perform tandem operations in supplying and mixing reagents as needed. When an analysis of the sample in reaction vessel 22 is completed, the reaction vessels are removed from the transport means 24 by vessel disposal means 15.

A photometric measuring means 38, located beneath the reagent arm 34 and beneath the reaction vessel transport means 24, measures light absorbency occurring at various wavelengths during transmission of light through the reaction fluid contained the reaction vessel 22. A source lamp 40 emits a light beam which passes through various lens housed in a photometer arm 42 to a photodetector 44 which, being mounted on the outer-end of the photometer arm 42 adjacent the outer periphery of the reaction vessel 22, rotates about the reaction vessel transport means 24. Using techniques well known in the art, photometric measuring means 38 relays absorbency readings to the computer 12 where the readings are converted into concentration units and displayed on display means 11 or printout 13.

Figure 5:
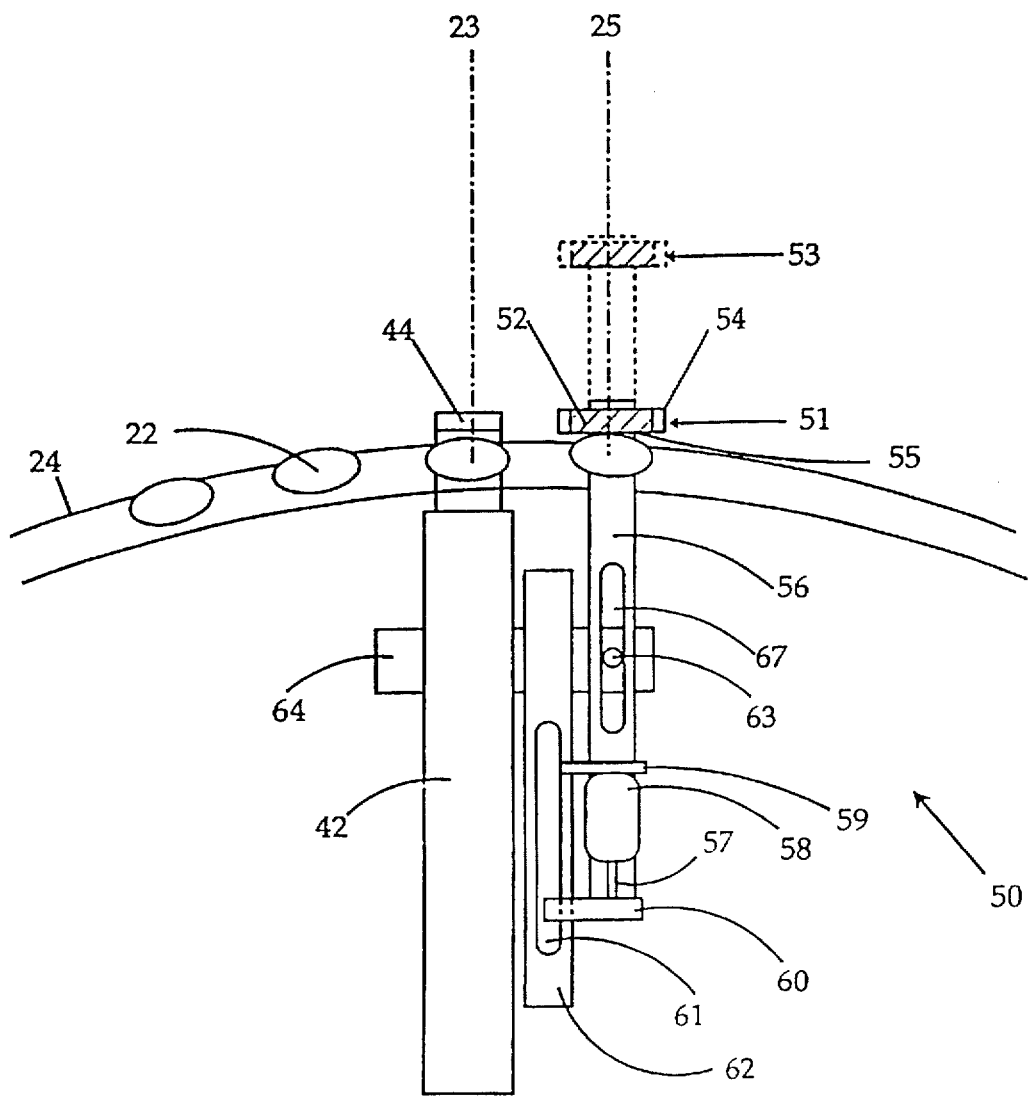
FIG. 5 is a fragmentary plan view of a reaction monitoring arm and of a source of a magnetic field that may be used with this invention.
Figure 6:
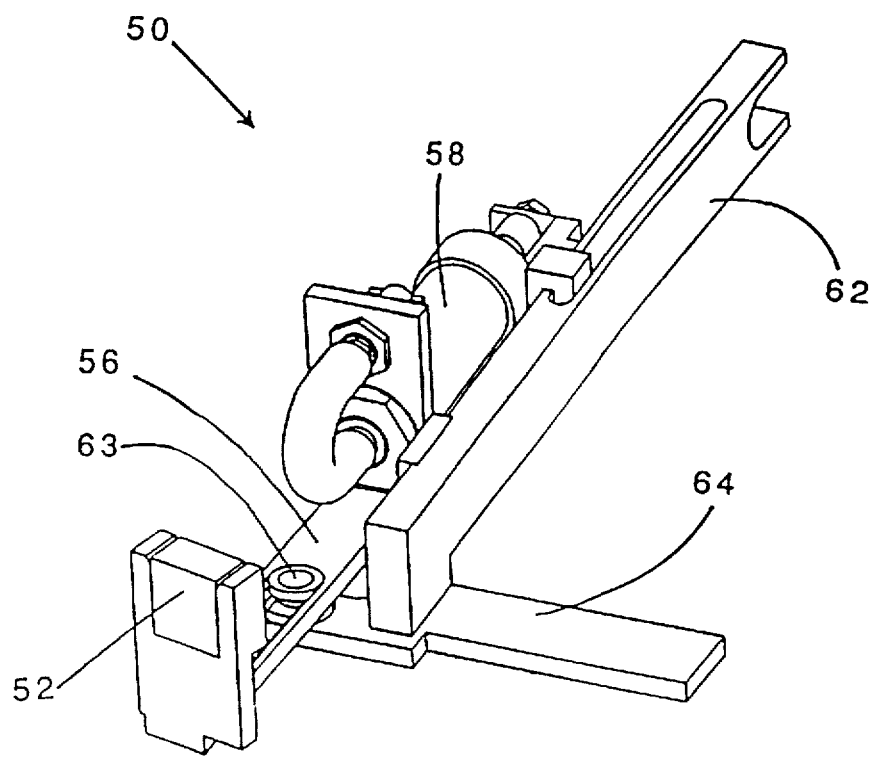
FIG. 6 is a pictorial view of a source of a magnetic field of this invention.

FIG. 5 shows a key feature of the present invention whereby a magnetic positioning means 50, secured to photodetector arm 42, acts to position a source of a magnetic field, preferably a magnet 52, such that the flux axis of the magnet 52 passes through approximately the bottom center of each reaction vessel 22 and attracts magnetic particles, contained within the reaction vessel and which act as a solid phase support for heterogeneous diagnostic assays, toward the sidewall thereof. Magnet 52 is shaded for purposes of illustration only and not to indicate cross-sectioning. Magnetic particles used to form magnet 52 are preferably chromium dioxide particles having a surface area of about 40 $m^2/gm$. Magnet 52 has a flat rectangular surface 55 and is mounted within an opening in mounting block 54 such that surface 55 is generally parallel to a reaction vessel 22 at position 25, which it is facing. Mounting block 54 is formed of a suitable engineering plastic or non-ferrous material. The center of the magnet 52 is positioned about at the same horizontal plane as is the bottom of reaction vessel 22. Mounting block 54 is mounted in a conventional manner on a support arm 56 which has at its upper end in the drawing an alignment groove 67 which engages an alignment post 63 secured to a cross member 64. The cross member 64 is secured to the photometer arm 42. The lower end (in the drawing) of the support arm 56 is secured to retainer 60 (by a screw not shown) which is slideably attached to a beam 62 by a groove in retainer 60 which engages an alignment rod 61. Beam 62 is attached to a cross member 64 which in turn is secured to photometer arm 42 of photometric measuring means 38.

As best seen in FIG. 5, an actuator 58 is attached to beam 62 through a linkage 59. Thus the actuator 58, when actuated by the computer 12, has an extendable actuating rod 57 secured to the retainer 60. When the actuator is activated, when actuating rod 57 moves retainer 60 along alignment rod 61, thus moving support arm 56, guided by pin 63 and alignment rod 61, radially over alignment post 63 thereby bringing magnet 52 proximate the processing position 25 of reaction vessel 22 between the two positions 51 and 53.

Position 51 is preferably in contact with the reaction vessel 22 at a position to provide an effective magnetic field. This is referred to as an effective magnetic position. Actuator 58 is adapted such that when not activated, actuating rod 57 is retained within actuator 58, so that support arm 56 is moved radially outward to position magnet 52 at position 53. In this position magnet 52 provides an ineffective magnetic field to the reaction vessel 22 and any particles therein. A "magnetically effective position" is defined as that position of magnet 52 (position 55) required to produce a "magnetically effective magnetic field," i.e., a magnetic field in the range 2000–5000 gauss, preferably about 3000 gauss measured at the center of a radially adjacent reaction vessel 22. A "magnetically ineffective position" is defined as that positioning of magnet 52 (position 53) that produces a "magnetically ineffective magnetic field," i.e., a magnetic field of strength less than about 50 gauss measured at the center of a radially adjacent reaction vessel 22. Actuator 58 is preferably an air-operated cylinder similar to that commercially known as "Airpot" and is available from the Airpot Corporation, Norwalk, Conn.

Radial positioning of magnet 52 at positions 51 and 53 is accomplished by means of pressurized air supplied in a conventional manner to actuator 58 from a small diaphragm type air pump (not shown). To deactivate the actuator 58, the pump is turned off and an exhaust valve opened, thereby releasing pressure so that the actuator rod 57 returns to its original position relative to actuator 58.

The source of the magnetic field is preferably a permanent magnet 52 of neodymium/iron/boron composition having a magnetic strength of approximately 3000 to 3500 gauss measured on the face of the magnet 52, and is rectangularly shaped, approximately 0.5 inch in length and 0.25 inches in thickness. Other sizes, shapes, materials and strengths may be used as decreased.

In operation, photometric measuring means 38 is conventionally controlled by the computer 12 of the clinical chemistry system 10 to assume a position at a first reaction vessel processing position designated hereinafter as 23 and illustrated by a dot-dash line in FIG. 5. Magnet 52, by its being within mounting block 54 and slideably attached to photometric measuring means 38 (photodetection arm 42), is positioned at the second reaction vessel processing position, next adjacent to and to the angular right (in the drawing) of the first reaction vessel processing position 23, designated hereinafter as 25 (also illustrated by a dot-dash line in FIG. 5).

An advantage of the present invention is the improved utility of magnet 52 in attracting the magnetic particles contained within reaction vessel 22, out of suspension and against the side-wall of the reaction vessel 22. This improvement is achieved by firstly positioning magnet 52 closely adjacent to or in contact with (position 51) reaction vessel 22 to provide a magnetically effective field, at processing position 25 for a first time interval T1 greater than a time interval required to effect a partial magnetization, or "pre-magnetization," of the magnetic particles. This results in a partial clumping together of the magnetic particles. A feature of the invention is that the first time interval T1, which must produce a partial magnetization of the particles, must be less than the time interval required to effect a substantially complete separation of the particles from the dispersion. At the partial "pre-magnetization" stage, smaller individual magnetic particles are attracted to one another and effectively form larger "particles" from the individual magnetic particles.

Secondly, removing the source of magnetic field to a distance from the processing position (position 53) to produce a magnetically ineffective magnetic field within the reaction vessel 22 for a second time interval T2. The time interval T2 is not critical and may accommodate system timing needs. Thirdly, positioning magnet 52 proximate the processing position 25, preferably at position 51, for a third time interval T3 greater than a time interval required to effect a complete separation of the particles from the dispersion. It had previously been considered disadvantageous that a pre-magnetization of the magnetic particles into larger "particles" occur because gravitational effects may cause the larger "particles" to settle out of solution faster thereby requiring a resuspension. In contrast, in the present invention, the pre-magnetization of individual particles into larger "particles" achieved during the first time interval T1 permits a more rapid final separation to be completed during the third time interval T3. It has been determined that the same degree of separation of magnetic particles from liquid solution, known in the prior art to require about 30 seconds, can be achieved by the method of the present invention by preferably utilizing first and third magnetic separation time intervals T1 and T3, respectively, in the range 2 to 8 seconds, preferably about 4 seconds each, separated by a second time interval T2 in the range 6 to 12 seconds, preferably about 8 seconds.

In addition to reducing the overall time required to affect separation, a further advantage of the present invention is that the system 10 is free to perform additional and unrelated diagnostic activities relative to reaction vessel 25 during the second time interval T2 thereby improving overall system throughput. After the third time interval T3, magnetic separation is complete and reagent probe 36 removes supernatant from the reaction vessel 25 position and transfers it to reaction vessel 23. These may be read by the photometric measuring means 38. Reaction vessels 23 and 25 may be any next adjacent positions on sample transport means 24, to where the reagent probe 36 and reagent arm 34 are accessible.

Although the chemistry system 10 may be programmed in any desired manner, the following description of an operation for performing a digoxin assay is given as illustration of the present invention. Similar program commands are used in conjunction with other diagnostic assays.

EXAMPLE 1

Enzymometric Immunoassay for Digoxin

The reagents described below are available commercially under the tradename DGNA Flex™ reagent cartridge 28 which is intended for the detection of digoxin in human specimens using the DuPont Dimension(r) clinical chemistry system.

Figure 3:
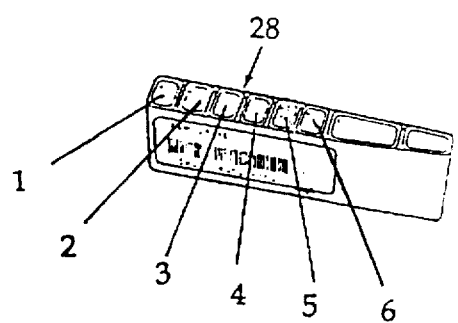
FIG. 3 is a pictorial perspective view of a reagent supply which is used in the automatic clinical chemistry system of FIG. 1.

1. Antibody-Beta-Galactosidase Conjugate Reagent, hereafter designated Conjugate, is a covalently cross-linked aggregate of antidigoxin antibody and beta-galactosidase. As seen in FIG. 3, the Conjugate solution is contained in wells designated as 1 and 2 of DGNA Flex™ reagent cartridge 28.

2. Chromium Dioxide Particle Reagent, hereafter designated CPR, being a suspension of magnetizable particles, preferably chromium dioxide particles having a surface area of about 40 $m^2$/gm, on which a coating of an appropriate biologically reactive substance, in the present example a covalent coating of ouabain-bovine serum albumin molecules, has previously been introduced. CPR is contained in wells designated as 3 and 4 of DGNA Flex™ reagent cartridge 28.

3. Chlorophenol red-B-D-galactopyranoside Reagent, hereafter designated CPRG, being a solution of cholorophenol red-B-D-galactopyranoside in a buffer is contained in wells designated as 5 and 6 of DGNA Flex™ reagent cartridge 28.

The following procedural method can be used to perform a digoxin assay using the apparatus of this invention in the clinical chemistry system 10.

Procedure

1. Prior to testing specimens containing an unknown concentration of digoxin, five calibrator samples are normally tested in a "Calibration" mode of the system. The "assigned values" of each calibrator is manually entered into the computer 12 before the tests. Appropriate calibrators and reagent cartridge 28 are loaded on the system 10. After the tests are completed, computer 12 automatically performs a mathematical regression using the signals and assigned-values of all five samples. The regression employs an algorithm known to those skilled in the art as "LOGIT function" and computes a series of "linearization coefficients" that are subsequently retained in memory within in computer 12.

2. A digoxin test is scheduled on computer 12. A sample specimen is placed in a sample well 19 and the DGNA Flex™ reagent cartridge 28 is loaded onto sample transport means 24 using shuttle 32. The sequence of events by which the system 10 performs the digoxin test follow.

3. Upon receiving commands to perform a digoxin test, the system 10 forms two reaction vessels 23 and 25 situated around the perimeter of the sample transport means 24. The sample transport means 24 is contained in a chamber not shown which is maintained at a constant temperature of 37 degrees C.

4. A 100 µL aliquot of Conjugate is automatically withdrawn from the DGNA Flex™ reagent cartridge 28 and dispensed into reaction vessel 23 by probe 36.

5. A 175 µL aliquot of CPRG is withdrawn from the DGNA Flex™ reagent cartridge 28 and disposed into reaction vessel 25 by the probe 36.

6. After 60 seconds, a 30 microliter sample of the specimen is withdrawn from the sample well 19 situated on sample transport means 24 and dispensed into reaction vessel 23 by probe 20. Probe 20 is vibrated ultrasonically for 2 seconds while immersed in the solution to provide thorough mixing of the specimen with the Conjugate solution.

7. After an incubation period of approximately 250 seconds, a 75 microliter aliquot of CPR suspension is withdrawn from the DGNA Flex™ reagent cartridge 28 and dispensed into reaction vessel 23 by probe 36 which is vibrated ultrasonically for about 3 seconds while immersed in the liquid to ensure consistent re-suspension of the CPR particles. After dispensing the suspension into reaction vessel 23, probe 36 is again vibrated for 2 seconds while immersed in the solution to achieve consistent suspension of the CPR in the reaction mixture.

8. The mixture is allowed to incubate for approximately 2 minutes during which the Conjugate molecules stoichiometrically bound to the digoxin molecules provided by the specimen remain in solution, while excess Conjugate is bound by a Ouabain-BSA coating on CPR particles.

9. Approximately 2 minutes after the dispensing of CPR, photometer arm 42 moves to a position such that the permanent magnet 52 is directly facing reaction vessel 23 in position 51 in contact with reaction vessel 23 radially outward from sample transport wheel means 24.

10. Photometer arm 42 supporting permanent magnet 52 in position 51 is held stationary for first time interval T1, preferably about 4 seconds, previously determined to be required for the magnetic field associated with magnet 52 to partially magnetize the CPR and, in effect, begin aggregation of the magnetic particles. After first time interval T1, actuator 58 is deactivated to move arm 56 radially outward causing magnet 52 to take position P2 displaced radially outward from sample transport wheel means 24 a magnetically ineffective distance previously determined to be required for the magnetic field associated with magnet 52 to have negligible magnetic effect on the CPR particles, preferably a distance of about 0.75 inches.

11. During a second time interval T2, previously determined as allowing only negligible settlement of the partially magnetized CPR particles from the previous consistent suspension of CPR in the reaction mixture, preferably about 8 seconds, photometric measuring means 38 is available to perform other diagnostic tests. During second time interval T2, additional photometric tests may be readily accomplished, thereby enabling an effective increase in the overall system 10 productivity.

12. After second time interval T2 is completed, photometer arm 42 supporting magnetic positioning means 50 is returned to a position in alignment with reaction vessel 22A. Actuator 58 is activated to move arm 56 radially inward causing magnet 52 to again take position P1 for a third time interval T3 previously determined as required to produce a complete separation of CPR particles, preferably about 4 seconds.

13. Reagent probe 36 is commanded to withdraw a 60 microliter microliter aliquot of liquid, now free of CPR particles, from reaction vessel 23 and dispense it into reaction vessel 25, for enzymatic measurement in reaction vessel 25. Excess Conjugate molecules are bound to the CPR and retained in reaction vessel 23.

14. After 25 seconds, the photometer arm 42 is moved to face reaction vessel 25. Absorbency at ten wavelengths are measured. The difference of absorbency between 577 nm and 700 nm is computed by the computer and recorded as rA (initial reading).

15. Twenty seconds after the initial reading, the photometric measuring means 38 measures the absorbency of reaction vessel 25 again. The difference of absorbency between 577 nm and 700 nm is computed and recorded as rB (second reading).

16. The difference between rB and rA is computed and recorded as the photometric signal of the test. The signal is used to compute the concentration of digoxin in the specimen by comparison with the results of the calibration procedure in Step 1.

A further advantage of the present invention arises from positioning magnet 52 at a magnetically ineffective position, i.e., position 53, during angular movement of photometric arm 42 relative to reaction vessels 22 located on sample transport means 24. In some of the prior art, magnet 52 was typically retained proximate reaction vessels 22 during angular movement of photometric arm 42. The relative movement to reaction vessels 22 during various incubation times caused premature aggregation of magnetic particles reagents possibly resulting in erroneous test results since an insufficient number of particles was available for excess antibody binding. Table 1 provides a comparison of residual particle absorbencies measured at 700 um in the instance that magnet 52 is maintained fixed in position 51 as compared to switching magnet 52 from position 51 to 53 as provided by the present invention.

TABLE 1

"Residual Particle Absorbency" Results

| Number of Magnetic Exposures | Magnet 52 Fixed At Position 51 | Magnet 52 Switched To Position 53 |
| --- | --- | --- |
| 1 | +82 | −19 |
| 2 | +32 | −20 |
| 3 | +32 | −20 |
| 4 | +20 | −20 |
| 5 | +18 | −20 |

As may be seen from Table 1, the readouts obtained when the magnet is switched to position 53 are low noise and constant regardless of the number of exposures. With the magnet fixed at position 51, the readings are noisy and vary with the number of exposures. Because the reaction vessels are positioned on the circumference of the reaction vessel transport means, they are necessarily in a singulated file, next adjacent one another. Consequently, in the prior art when a fixed position magnet was employed to effect magnetic separation, as the photometer arm bearing the fixed position magnet moved radially around the circumference, the magnetic field was operating on all the intervening reactions vessels. This had the undesirable effect of introducing a small but spurious premature magnetic separation of the sample within the reaction vessels exposed to the fixed position magnet. This premature separation produced an uncontrolled variable in the "residual particle absorbency" as given Table 1 for the magnet fixed at position 51. As further shown in Table 1, with the new capability of removing the magnet 52 away from the reaction vessels during movement of the photometric arm past the next adjacent reaction vessels of the present invention, the spurious "residual particle absorbency" is effectively reduced with the magnet in position 53.

What is claimed is:

1. A method for separating magnetically responsive particles from a liquid dispersion disposed in a reaction vessel, the method comprising:

providing a single magnet to subject the reaction vessel to a magnetically effective magnetic field for a first time interval, said first time interval being less than a time interval required to effect a complete separation of the particles from the dispersion;

subjecting the vessel to a magnetically ineffective magnetic field within the vessel for a second time interval; and, using said single magnet to subject the vessel to the magnetically effective magnetic field within the vessel for a third time interval greater than a time interval required to effect a complete separation of the particles from the dispersion.

2. The method of claim 1 wherein the magnetically effective magnetic field has strength in the range 2000 to 5000 gauss.

3. The method of claim 2 wherein the source of the magnetically effective field is a permanent magnet.

4. The method of claim 3 wherein the permanent magnet is composed of neodymium/iron/boron composition and has a magnetic strength of approximately 3000 to 3500 gauss measured on the face of the magnet.

5. The method of claim 4 wherein the magnetically responsive particles are coated with a biologically reactive substance.

6. The method of claim 1 wherein the magnetically ineffective magnetic field has strength less than 50 gauss.

7. The method of claim 1 wherein the magnetically responsive particles are composed of chromium dioxide.

8. The method of claim 1 wherein the first time interval and the third time interval are both in the range 2 to 8 seconds.

9. The method of claim 1 wherein the second time interval is in the range 6 to 12 seconds.

* * * * *

UNITED STATES PATENT AND TRADEMARK OFFICE
CERTIFICATE OF CORRECTION

PATENT NO. : 5,776,784
DATED : July 7, 1998
INVENTOR(S) : Joseph Edward Kegelman, et. al.

It is certified that error appears in the above-identified patent and that said Letters Patent is hereby corrected as shown below:

Column 10, Line 13: After "given" insert --in--.

Signed and Sealed this

Tenth Day of November 1998

Attest:

BRUCE LEHMAN

Attesting Officer    Commissioner of Patents and Trademarks